United States Patent [19]

Randall

[11] 4,317,034
[45] Feb. 23, 1982

[54] METHOD AND APPARATUS FOR MEASURING NEUTRON CHARACTERISTICS OF MATERIAL SURROUNDING A BOREHOLE

[75] Inventor: Russel R. Randall, Houston, Tex.

[73] Assignee: Dresser Industries, Inc., Dallas, Tex.

[21] Appl. No.: 163,260

[22] Filed: Jun. 26, 1980

Related U.S. Application Data

[63] Continuation-in-part of Ser. No. 156,971, Jun. 6, 1980.

[51] Int. Cl.³ .............................................. G01V 5/00
[52] U.S. Cl. .................................. 250/262; 250/270
[58] Field of Search ...................... 250/262, 269, 270

[56] References Cited

U.S. PATENT DOCUMENTS

| | | | |
|---|---|---|---|
| 3,379,882 | 4/1968 | Youmans | 250/262 |
| 3,379,884 | 4/1968 | Youmans | 250/262 |
| 3,566,116 | 2/1971 | Nelligan | 250/262 |
| 4,046,764 | 9/1977 | Marquis | 250/262 |
| 4,223,218 | 9/1980 | Jacobson | 250/262 |
| 4,267,447 | 5/1981 | Johnstone | 250/262 |

Primary Examiner—Alfred E. Smith
Assistant Examiner—Janice A. Howell
Attorney, Agent, or Firm—Richard M. Byron; Patrick H. McCollum

[57] ABSTRACT

A pulsed source of fast neutrons and a radiation detector system are utilized in a well logging instrument, the detector being responsive to the thermal neutron population decay rate. The inverse of the decay rate is proportional to the measured macroscopic neutron absorption cross-section (Sigma). A Sigma is calculated by taking the natural logarithm of the ratio of the detected radiation counts occurring within two measurement intervals of fixed duration and starting at a fixed time after the neutron burst. This Sigma measurement provides a feedback voltage which is used in altering the starting time of a single measurement interval in a subsequent source pulsing cycle to provide a measured Sigma value.

18 Claims, 6 Drawing Figures

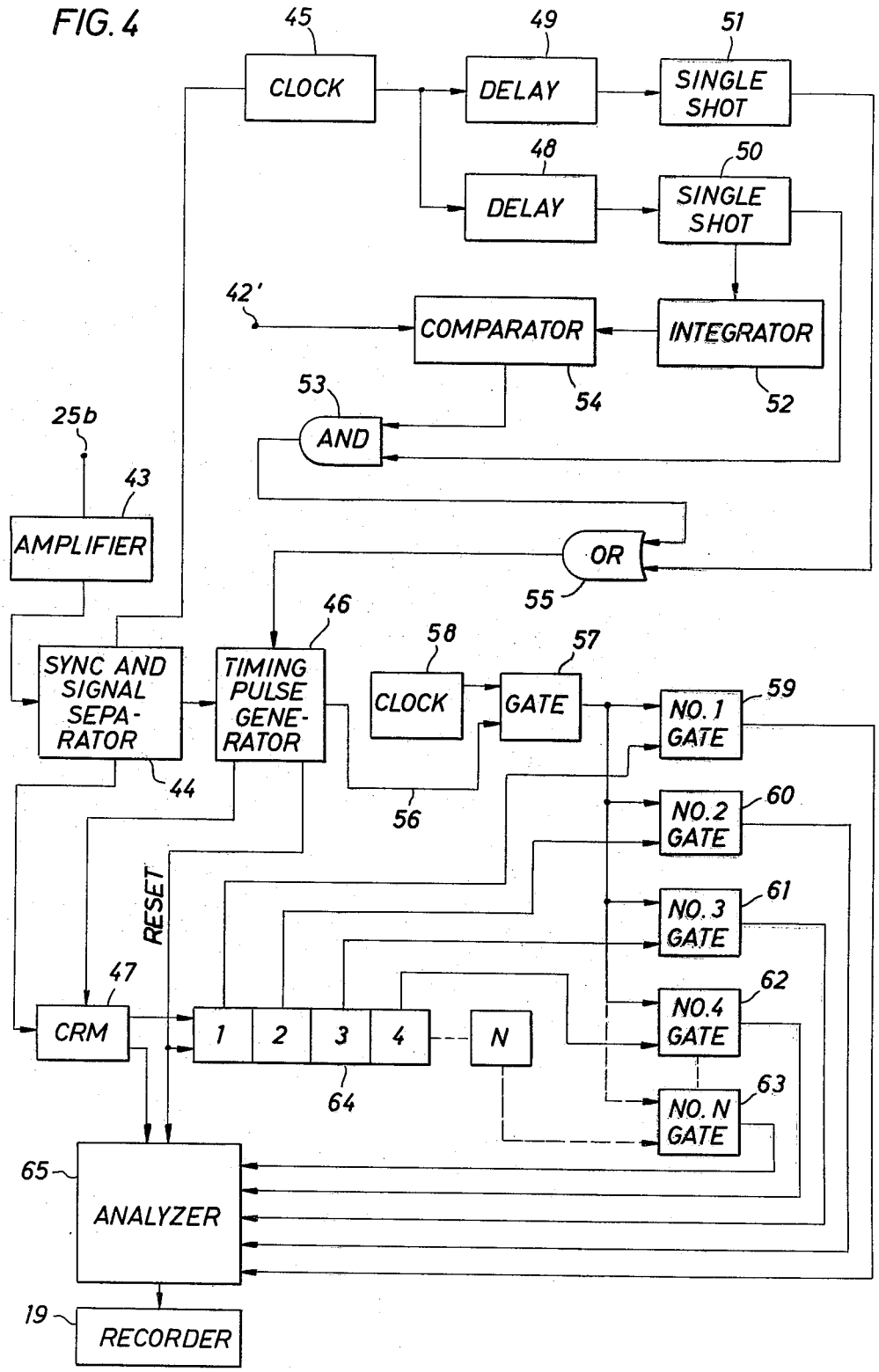

METHOD AND APPARATUS FOR MEASURING NEUTRON CHARACTERISTICS OF MATERIAL SURROUNDING A BOREHOLE

This application is a continuation-in-part of my co-pending application Ser. No. 156,971, filed June 6, 1980.

BACKGROUND OF THE INVENTION

This invention relates, in general, to radioactivity well logging, and more particularly to methods and apparatus for determining the macroscopic thermal neutron capture cross-section of the formations surrounding a borehole as determined by radiation measurements.

It is well known in the art of radioactivity well logging, for example, as illustrated and described in U.S. Pat. Nos. 3,379,882 and 3,379,884 which issued to Arthur H. Youmans and each of which is assigned to the assignee of the present invention, to measure the macroscopic thermal neutron capture cross-section [Sigma ($\Sigma$)] of the formations surrounding a borehole. This prior art method makes such a measurement or computation by measuring the decline of the thermal neutron population in such formations within a fixed period of time following the emission of a burst of high energy neutrons and by dividing the radiations indicative of such thermal neutrons into two equal groups and computing the rate of change over the selected time interval. In U.S. Pat. No. 3,566,116, use is made of two measurement intervals so that the starting time and the duration of the two measurement intervals can be continuously adjusted so as to maintain a fixed counting ratio between the two measurement intervals.

Yet another method of measuring the macroscopic thermal neutron capture cross-section of the formation is described in U.S. Pat. No. 4,046,764, which issued to Gerald L. Marquis and which is assigned to the assignee of the present invention. This method makes use of establishing the points in time of which radiation is detected within a fixed duration time interval beginning at a fixed time following each neutron burst from the source. A unique solution is obtained where each measured value of the time relationship defines a single value of macroscopic neutron absorption cross-section.

SUMMARY OF THE INVENTION

In the preferred embodiment of the present invention, a calculation of the measurement of the decline of the thermal neutron population in the formation is derived by counting the detected radiation within two equal measurement intervals of fixed time duration and occurring at a fixed time after the neutron burst. A ratio of the two counting rates provide the rate of change over the selected time interval. The counting ratio is converted into a natural logarithm representative of the Sigma calculation.

The Sigma calculation derived by the ratio of the two fixed measurement intervals is utilized to vary the starting time of a single, fixed duration, measurement interval in a subsequent source pulsing cycle. In the preferred embodiment the measurement interval will begin no earlier than 200 microseconds following the neutron burst and no later than 400 microseconds following the neutron burst. The measurement interval will be 600 microseconds in duration. The precise points in time at which radiation is detected within the interval following each neutron burst is established. Each measured value of the time relationship of the pulses will define a single value of the macroscopic neutron absorption cross-section. This measurement is recorded representing the macroscopic thermal neutron capture cross-section of the formation material.

Accordingly, it is a feature of the present invention to provide new and improved methods and apparatus for determining a macroscopic thermal neutron cross-section of formations surrounding earth boreholes;

It is also a feature of the present invention to provide new and improved methods and apparatus for varying the start time for the measurement interval used in determining a macroscopic thermal neutron cross-section;

It is yet another feature of the present invention to provide methods and apparatus for utilizing a macroscopic thermal neutron cross-section calculation for altering the starting time of the measurement interval within succeeding neutron source pulse cycles; and Still another feature of the present invention is to calculate the formation Sigma based on a ratio of the counting rates within two contiguous fixed measurement intervals and to use that Sigma calculation to set the starting time of a single, fixed duration measurement interval on a subsequent measurement cycle.

These and other features and advantages of the present invention can be understood from the following description of the techniques of producing the invention described in conjunction with the following drawings:

BRIEF DESCRIPTION OF THE DRAWINGS

FIG. 4 illustrates in block diagram additional surface electronics in accordance with the present invention.

DETAILED DESCRIPTION OF THE DRAWINGS

Figure 1:
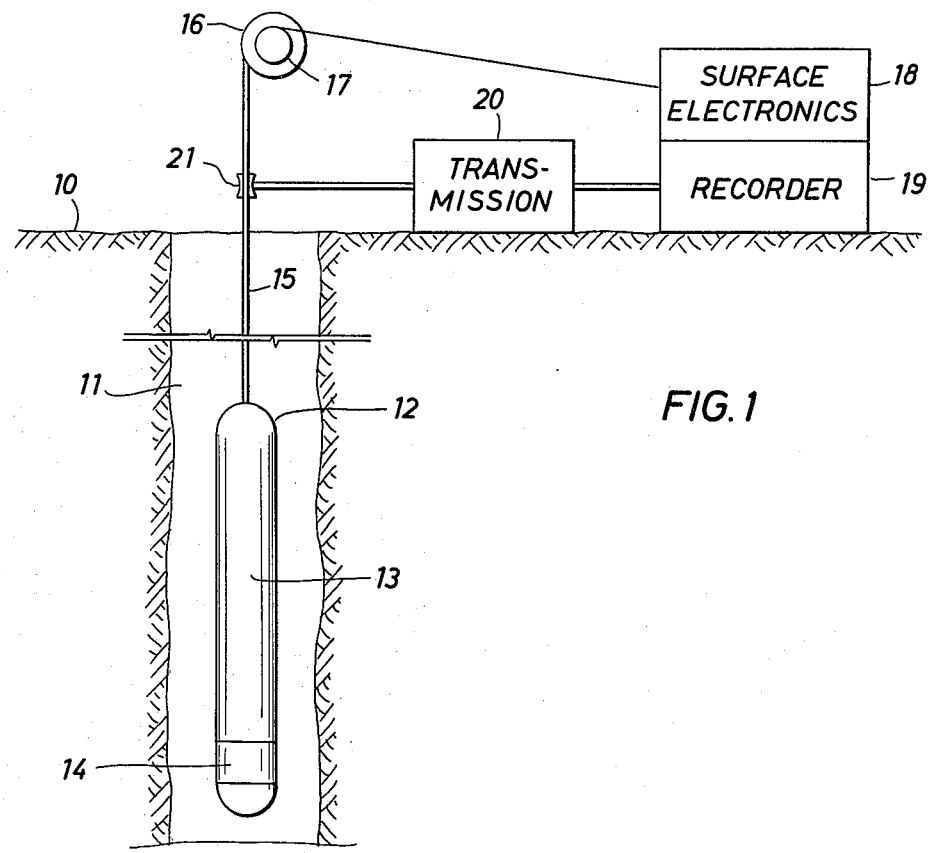
FIG. 1 is a side elevational view, partly in cross-section, of a radioactivity logging system in accordance with the present invention.

Referring now to the drawings in detail, particularly to FIG. 1, there is illustrated schematically a radioactivity well surveying operation in which a portion of the earth's surface 10 is shown in vertical section. An earth borehole 11 penetrates the earth's surface and may or may not be cased. Disposed within the well is subsurface instrument 12 of the well logging system. Subsurface instrument 12 comprises a detecting system 13 and a pulsed neutron source 14 for irradiating the formation with high energy neutrons. Cable 15 suspends the instrument 12 in the well and contains the required conductors for electrically connecting the instrument with the surface apparatus. The cable is wound on or unwound from drum 16 in raising and lowering the instrument 12 to traverse the well.

In making a radioactivity log of a well, instrument 12 is caused to traverse the well. Thereby neutrons from source 14 pulsedly irradiate the formations surrounding the borehole, and radiations influenced by the formations are detected by the detecting system 13. The resultant signal is sent to the surface through conductors within cable 15. Through slip rings and brushes 17 on the end of drum 16, the signals are coupled into surface electronics 18. After processing by the circuitry hereinafter described and illustrated, the resulting information is recorded on recorder 19. Recorder 19 is driven through transmission 20 by a measuring reel 21 over which cable 15 is drawn so that recorder 19 moves in correlation with the depth as instrument 12 traverses the well. The elements are shown diagrammatically, and it is understood that the associated circuits and power supplies are provided in a conventional manner. It is also understood that the housing for instrument 12 is constructed to withstand the pressures and mechanical and thermal abuses encountered in logging a deep well and to provide adequate space within it to house the necessary apparatus and to permit the transmission of radiation therethrough.

In the operation of the apparatus of FIG. 1, the source 14 is periodically activated, for example, approximately eleven hundred microseconds causing the formation to be irradiated with high energy neutrons. Gamma rays are detected by the detector system 13 which are indicative of thermal neutron source burst. The number of gamma rays present at any time is proportional to the thermal neutron population around the instrument 12. The decay rate of the neutron population is an exponential. Electrical signals are transmitted up cable 15 indicative of such detected gamma radiation.

Figure 2:
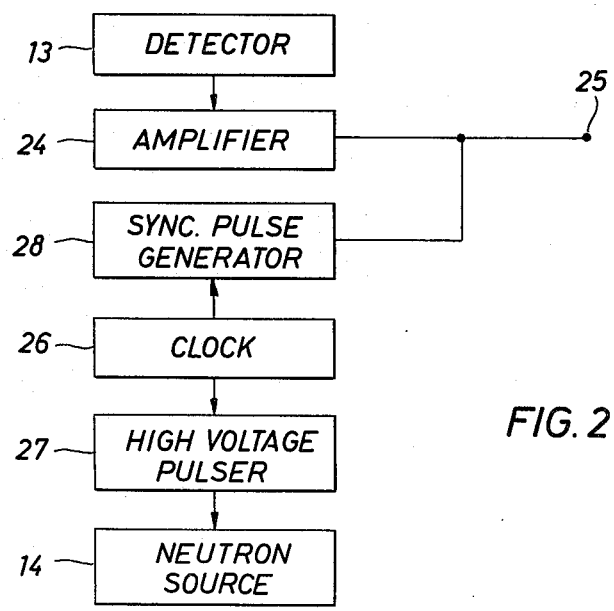
FIG. 2 illustrates in block diagram the subsurface electronics in accordance with the present invention.

Referring now to FIG. 2, there is illustrated the subsurface circuitry for generating the sync signals and signal pulses hereinafter illustrated and described. The detector 13 is coupled to an amplifier 24, whose output is connected to a high voltage pulser 27 which drives a conventional neutron source 14. In the preferred embodiment of the present invention, source 14 is a conventional D-T accelerator producing high energy 14 Mev neutrons at a rate as determined by the clock 26. The discrete burst of neutrons occur 1000 microseconds apart and are generally of 10 to 50 microseconds duration. Clock circuit 26 also drives a sync generator 28 having its output connected to junction 25. The junction 25 is connected to a conductor of cable 15 and serves to carry the signals to surface electronics 18 for processing.

In the operation of the circuitry and apparatus illustrated in FIG. 2, the clock 26 causes high voltage to be applied to neutron source 14 to generate discrete bursts of neutrons, each such burst being separated by approximately 1000 microseconds. The detector 13 detects gamma radiation resulting from the capture of thermal neutrons occasioned in the formation surrounding the borehole by neutron source 14. The detected pulses from detector 13 are immediately amplified by amplifier 24 and combined with the sync pulses, generated by sync pulse generator 28 in response to clock 26, for transmission to the earth's surface.

Figure 3:
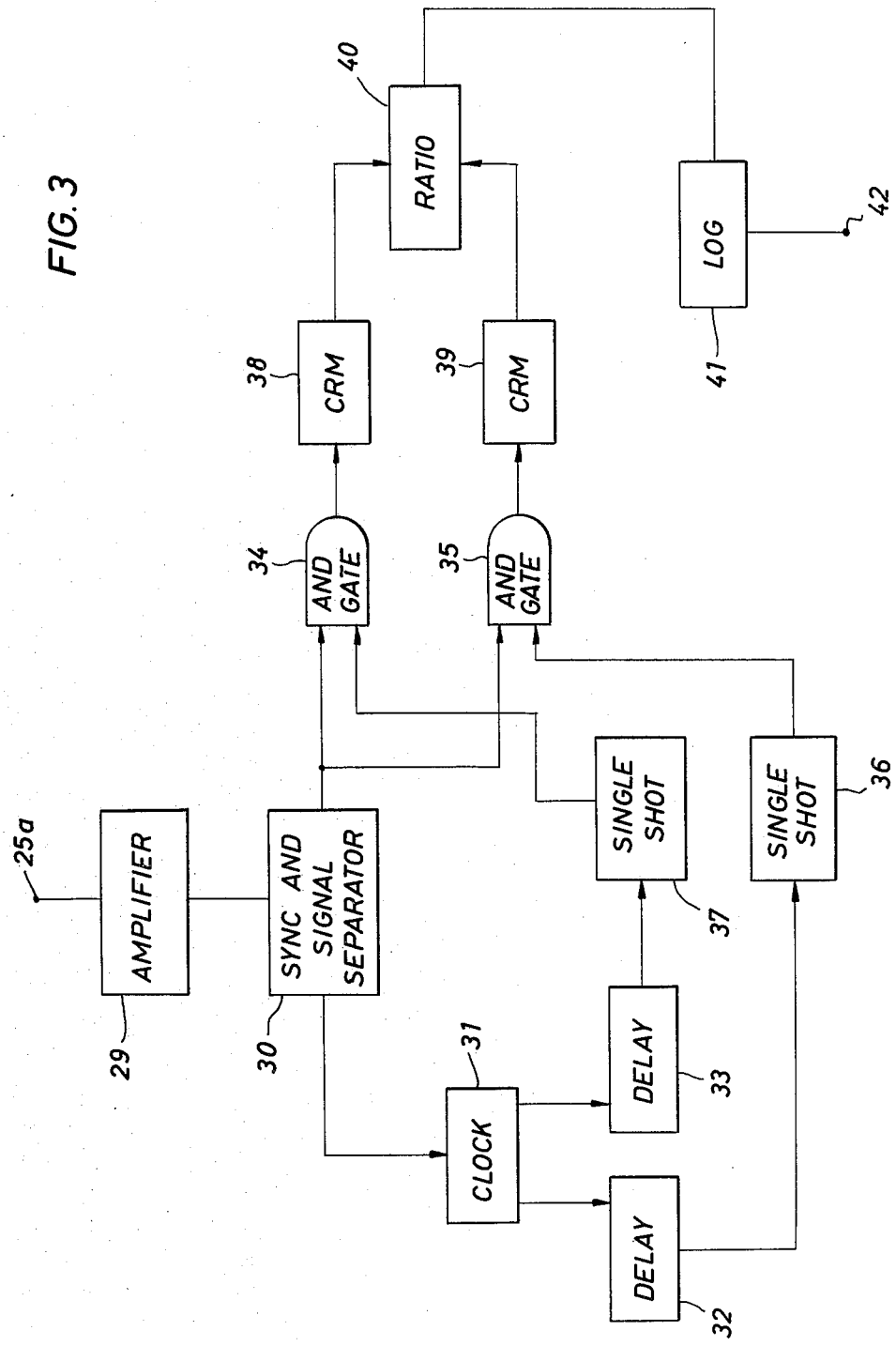
FIG. 3 illustrates in block diagram a portion of the surface electronics utilized in accordance with the present invention.

Referring now to FIG. 3, the surface electronics shown generally by the reference numeral 18 in FIG. 1 is shown in greater detail. The junction 25 corresponds to the junction 25 in the subsurface circuitry. Junction 25a is coupled through an amplifier 29 to a conventional sync and signal separator circuit 30 which separates the sync signal from the amplified signal pulses. The separation can be achieved by any of the conventional circuit devices, for example, through pulse height discrimination. The sync output of the separator circuit 30 is coupled into clock circuit 31 the output of which is connected to the input of delay circuits 32 and 33. The signal output of separator circuit 30 is coupled into one input of a two-input AND gate 34 and into one input of a second two-input AND gate 35.

Delay circuit 32 is set to have a delay of 400 microseconds and has the output connected to single shot multivibrator 36. Delay circuit 33 is set to have a delay of 600 microseconds and has the output connected to single shot multivibrator 37. Each of the single shot multivibrators 36 and 37 produces a square wave of 200 microseconds duration. The output of single shot multivibrator 36 is connected to the second input of AND gate 35 while the output of single shot multivibrator 37 is connected to the second input of AND gate 34. The output of AND gate 34 is connected to count rate meter 38 and the output of AND gate 35 is connected to count rate meter 39. The outputs of count rate meters 38 and 39 provide the inputs to ratio circuit 40 the output of which is connected to logarithmic circuit 41. The output of logarithmic circuit 41 is connected to junction 42.

In a homogeneous medium, the rate of thermal neutron absorption is defined by the following equation:

$$N_2 = N_1 e^{-\frac{\Delta t}{T}} \tag{1}$$

where $N_1$, $N_2$ are the number of thermal neutrons in existence at times $t_1$, and $t_2$; $\Delta t$ is the time between measurements $(t_2 - t_1)$; and T is the absorption rate of thermal neutrons in the medium.

Thermal neutron capture cross-section of the medium is determined from the rate of absorption as follows:

$$\Sigma = \frac{1}{VT} \tag{2}$$

where $\Sigma$ is the thermal neutron capture cross-section and V is the velocity of thermal neutrons. Solving for Sigma yields the familiar equation:

$$\Sigma = \frac{1}{V\Delta t} \ln \frac{N_1}{N_2} \tag{3}$$

Figure 5A:
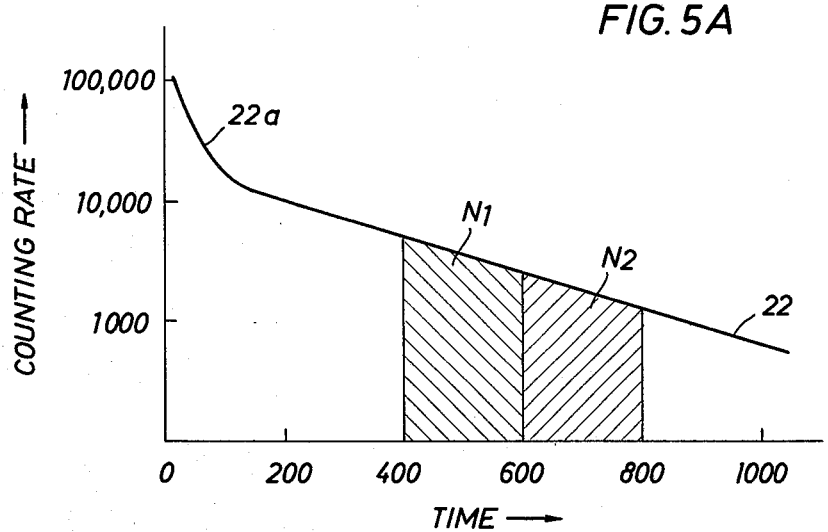
FIG. 5A is a schematic representation of the characteristic decay of a thermal neutron population following a burst of fast neutrons within a well and a method of utilizing two gates to provide a measurement of the rate of decline of the population.

Referring now to FIG. 5A, there is graphically illustrated a waveform 22 which is representative of the rate of neutron decay as measured by detector system 13 in accordance with the present invention. With the data which produces such curves, the rate of decline of the thermal neutron population is computed by measuring the integrated radiation counting rate under the curve 22 occurring during measure intervals $N_1$ and $N_2$. $\Delta t$ is measured between the midpoints or starts of the two measurement intervals and V is set to a constant value of 2200 meters/second. This is sufficient data to calculate Sigma.

In the operation of the surface electronics illustrated in FIG. 3, the sync signal and the detected radiation pulses are provided by subsurface instrument 12 to amplifier 29. The amplified output of amplifier 29 is coupled to sync and signal separator circuitry 30 the sync output of which is coupled to clock circuit 31 and the signal output representative of the detected radiations is connected to one input of AND gates 34 and 35. The clock output signal from clock circuit is delayed 400 microseconds by delay circuit 32 and is delayed 600 microseconds by delay circuit 32 and is delayed 600 microseconds by delay circuit 33. The delayed clock signal output from delay circuit 32 is coupled to single shot multivibrator 36 while the delayed clock signal output from delay circuit 33 is coupled to single shot multivibrator 37.

Single shot multivibrators 36 and 37 are set to produce a square wave output of 200 microseconds in duration. The output of single shot multivibrator 36 provides the second input to AND gate 35 whereas the output of single shot multivibrator 37 provides the second input to AND gate 34. Thus, AND gate 35 will pass all the detected radiation occurring in the time interval from 400-600 microseconds following the sync pulse and AND gate 37 will pass all the detected radiation occurring in the 600-800 microsecond interval. The respective radiation intervals are illustrated by measurement intervals $N_1$ and $N_2$ of FIG. 5A.

The outputs of AND gate 34 and AND gate 35 are counted by count rate meters 38 and 39, respectively. A ratio is taken by ratio circuit 40 of the counts within the two measurement intervals. The logarithmic circuit 41 provides a natural logarithmic signal of the ratio signal from ratio circuit 40. The output of logarithmic circuit 41 is connected to junction 42 and is the Sigma value of the formation.

Referring now to FIG. 4, circuitry is described in block diagram in accordance with the present invention wherein the input terminal 25b corresponds with junction 25 of FIG. 2 and provides the input to amplifier 43. The output of amplifier 43 is connected to the input of sync and signal separator circuit 44. The sync outputs of sync and signal separator 44 are connected to clock circuit 45 and timing pulse generator circuit 46. The signal output of sync and signal separator circuit 44 is connected to the input of count rate meter 47.

The output of clock circuit 45 is connected to the inputs of delay circuits 48 and 49 the outputs of which are connected to the inputs of single shot multivibrators 50 and 51, respectively. One output of single shot multivibrator 50 is connected to integrator circuit 52 with the second output of single shot multivibrator 50 connected to one input of two-input AND gate 53. The output of integrator circuit 52 is connected to comparator circuit 54, the second input of which corresponds to junction 42 of FIG. 3.

The output of comparator circuit 54 is connected to the second input of AND gate 53 with its output connected to one input of two-input OR gate 55. The second input to OR gate 55 is connected to the output of single shot multivibrator 51. The output of OR gate 55 is connected to one input of timing pulse generator circuit 46. Timing pulse generator 46 has one of its outputs connected to a second input to count rate meter 47. Another output of timing pulse generator 46 is connected by conductor 56 to one input of gate circuit 57. Another input to gate 57 is driven by the output of clock 58. The output of gate 57 is connected to first input of each of a plurality of gates 59-63, also identified as gates No. 1, No. 2, No. 3, No. 4, and No. N, respectively.

The output of count rate meter 47 is connected into a conventional pulse detector circuit 64, for example, a pulse register having a plurality of outputs which are respectively connected to the second inputs of gates 59-63. Pulse detector circuit 64 recognizes the time sequence of the output pulses from count rate meter 47 and sorts them accordingly. Thus, the first pulse in the detection cycle is passed to No. 1 gate and the second pulse received is passed in a similar manner to No. 2 gate. By having an adequate number of places within pulse detector circuit 64 and a correspondingly adequate number of gates, a timing gate is thus turned on by each pulse detected in count rate meter 47 at a time coinciding with the time position of that pulse in the detection cycle. Following the end of the cycle, a reset pulse from timing pulse generator 46 returns pulse detector circuit 64 to its original condition. Output pulses from count rate meter 47 and reset pulses from timing gate generator 46 are also connected into analyzer circuit 65. The outputs of gates 59-63 are also connected into analyzer circuit 65.

In the operation of the portion of the surface electronics illustrated in FIG. 4, it should be appreciated that the input signal appearing at input terminal 25b consists of a trigger or sync pulse followed by the signal pulses of interest. The trigger pulse is synchronized with the neutron burst from the subsurface instrument source 14. The signal pulses are random but on the average decrease in number exponentially with time. A relatively few follow each neutron burst varying from zero to probably less than ten in number. This number is a function of instrument efficiency and well bore environment. Although the circuitry illustrated utilizes gates No. 1, 2, 3, 4 through N, any number of gates can be used to accept the required number of pulses per cycle.

The input signal is amplified by amplifier circuit 43 and the sync signal is separated from the pulse signal by sync and signal separator circuit 44. The sync output is coupled to clock circuit 45 and timing pulse generator 46, and the signal output representative of the detected radiations is connected to the input of count rate meter 47. The clock output signal from clock circuit 45 is delayed 200 microseconds by delay circuit 48 and is delayed 400 microseconds by delay circuit 49. The delayed clock signal output from delay circuit 48 is coupled to single shot multivibrator 50 while the delayed clock signal output from delay circuit 49 is coupled to single shot multivibrator 51.

Single shot multivibrator 50 produces a square wave of 200 microseconds in duration which provides the input to integrator circuit 52. The square wave input to integrator circuit 52 is converted to a voltage level in the form of a d.c. voltage ramp which is proportional over time to the width of the input gate. The slope of the integrator output ramp can be set to provide the desired time constant for optimum use in comparator 54. In addition to the d.c. voltage input from junction 42', which is a d.c. voltage level proportional to the calculated Sigma of the measured formation. The source of the Sigma measurement at junction 42' is the portion of the surface electronics illustrated in FIG. 3 which is the Sigma calculated within the fixed measurement intervals of 400-600 microseconds and 600-800 microseconds.

Comparator circuit 54 will produce an output signal when the Sigma level and the integrator voltage level are in coincidence. The comparator output is connected to one input of AND gate 53, the second input being the 200 microsecond gate output from single shot multivibrator 50. AND gate 53 will produce an output whenever there is coincidence within comparator 53 and this coincidence occurs within the interval from 200-400 microseconds following the sync pulse. The output of AND gate 54 is connected to one input of OR gate 55 the second input being a 200 microsecond gate signal starting 400 microseconds after the sync signal. If OR gate 55 is not triggered by an output from AND gate 53, single shot multivibrator 51 will cause OR gate 55 to output a signal at the 400 microsecond point in time after the sync pulse.

The output signal from OR gate 55 is connected to timing pulse generator 46. Timing pulse generator 46 accepts the trigger pulse and generates time oriented logic signals for the other circuit blocks. For example, if the desired signal pulses fall within a 600 microsecond interval, with a starting time from between 200-400 microseconds following the sync pulse, the following logic is generated:

A. A 600 microsecond "gate on" signal coupled into count rate meter 47 from timing pulse generator 46;

B. A 600 microsecond "gate on" signal coupled into gate 57 by means of conductor 56 to thereby couple out the clock pulses from clock 58 to the inputs of gates 59-63.

C. A reset pulse coupled out of timing pulse generator 46 into the inputs of pulse detector circuit 64 and analyzer circuitry 65.

The preferred embodiment contemplates the use of a 5 MHz clock 58 which is used as the digital time reference for the measurement of the time relationship of the detected radiation pulses. The basic frequency of the clock is not critical; the value selected is determined by the desired accuracy in the measurement of the time relationship. The "gate on" pulse from timing pulse generator 46 into gate 57 enables the clock pulses to be used to operate gates 59-63. By way of example, clock gate 57 is open for a 600 microsecond period and the 5 MHz clock pulses are applied to the timing gate circuits during this period. Gates 59-63 are in the off condition at all other times.

Count rate meter circuit 47 is in the off condition except when turned on by logic from timing pulse generator 46, in this example, for 500 microseconds starting between 200-400 microseconds following the trigger sync pulse. When turned on, the count rate meter circuit 47 accepts signal pulses from sync and signal separator circuit 44. The pulses detected are processed in two fashions. They are shaped and integrated with an appropriate time constant to produce an analog signal proportional to the pulse rate. In addition, each signal pulse is shaped and passed as a gating pulse to pulse detector circuit 64.

The timing gates 59-63 are in the off position until the information begins, determined by an output from OR gate 55, and the clock pulses are impressed on the inputs of gates 59-63. When the first signal pulse occurs and is detected by the pulse detector circuit 64, No. 1 gate 59 is turned on and remains on throughout the measure cycle. The output of No. 1 gate is clock pulses equivalent to the time $600-T_1$, where $T_1$ is the time difference between the beginning of the information cycle and the detection of the first signal pulse. A later, second pulse will open No. 2 gate and produce a signal $600-T_2$ and so on with the remainder of other gates 61-63. At the end of the measure cycle, the clock gate 57 cuts off the timing pulses to timing gates 59-63. The outputs of gates 59-63 are coupled into analyzer circuit 65.

Analyzer circuit 50 contains means for counting the total number of clock pulses appearing in the combined inputs during a given cycle and also circuitry for converting the total digital count into an analog signal. The analyzer circuitry 65 is reset by means of the signals appearing on the reset input coming from timing pulse generator 46. Analyzer circuit 65 processes the input clock pulses based upon the unique relationship between Sigma and the pulse distribution. This relationship can be expressed as follows:

$$T_{otp} = > F(\Sigma, G, B)$$

where T is the operator, tp is based upon the individual pulse times, F represents the functional relationship, $\Sigma$ is the macroscopic capture cross-section, G is the gate width and B is the background radiation. The gate width is of a predetermined fixed duration and the background radiation can be removed by one of the well known background subtraction methods. Therefore, there is a unique Sigma value for every distribution of the detected radiation pulses whether the distribution be determined as the arithmetic mean tine, the medium time, or a weighted average.

Figure 5B:
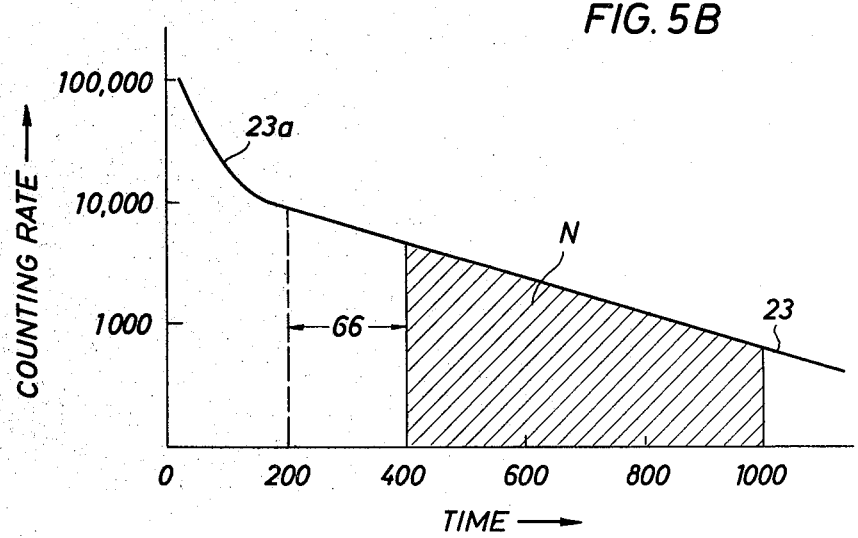
FIG. 5B is a schematic representation of the characteristic decay of a thermal neutron population following a burst of fast neutrons within a well and a method of utilizing a single, variable starting gate to provide a measurement of the rate of decline of the population.

Returning now to FIG. 5, the rate of neutron decay curves, 22 and 23, have an initial rate of neutron decay, 22a and 23a, which is not an exponential function but rather is relatively a complex function caused in part by borehole influences. After some short period of time these disturbing influences become negligible and the rate of decay is substantially controlled by the formation capture cross-section. The point at which the undesirable influences become negligible is related to the rate of decline in the neutron population. To increase measurement accuracy, partly based on a higher counting rate of detected radiation, it is desirable to begin counting the detected radiation early on the exponential portion of the decay curve. Therefore, as the calculated Sigma value for the formation increases as supplied from the two fixed measurement intervals, it is desirable to reduce the point in time on the rate of decay curve at which the measurement of detected radiation begins.

As discussed in relation to the circuit drawings, the starting time in relation to the sync pulse is altered by a function of the previously calculated Sigma value. The measure interval N is caused to begin by an output provided from AND gate 53 which can range as early in time as 200 microseconds following the sync pulse. If AND gate 53 does not provide an output signal, OR gate 55 will assure the measure interval to begin no later then 400 microseconds following the sync pulse. In other words, measure interval N will begin within time interval 66 illustrated in FIG. 5B.

Thus, there has been described and illustrated herein a new and improved method and apparatus for measuring thermal neutron decay times. Those skilled in the art will recognize that numerous other variations and modifications may be made without departing from the scope of the present invention. For example, delay circuit 32 could be set to provide calculation intervals which will not be contiguous but rather would be separated by some fixed time. Likewise, the time delay Sigma value could also be derived from a single gate time relationship Sigma calculation.

The embodiment of the invention in which an exclusive property or privilege is claimed are defined as follows:

1. A method for logging the formations surrounding an earth borehole, comprising:

pulsedly irradiating said formations with discrete bursts from a source of high energy neutrons;

detecting radiations emanating from said irradiated formations at a detector spaced from said source;

measuring said detected radiations during first and second time intervals following a burst from said source;

generating time-separated electrical pulses indicative of said detected radiations during a third fixed time duration interval following a subsequent burst from said source; and controlling automatically the starting time of said third measurement interval in accordance with the said measurement from said first and second time intervals.

2. The method of logging of claim 1 wherein said thrid time interval is automatically controlled to start from between 200–400 microseconds following said subsequent neutron burst.

3. The method of logging of claim 2 wherein said third time interval is of 600 microseconds in duration.

4. The method for logging of claim 3 wherein said first and said second time intervals are contiguous and of equal duration.

5. The method for logging of claim 4 wherein said first time interval is from between 400–600 microseconds after said burst of high energy neutrons and said second time interval is from between 600–800 microseconds following said burst of high energy neutrons.

6. The method for logging of claim 5 further comprising deriving a ratio of said measured radiations during said first and second intervals, said ratio being substantially representative of the decline of the neutron population in said formations.

7. The method for logging of claim 6 further comprising generating an electrical signal representative of the arithmetic mean time of the total of said electrical pulses within said third time interval.

8. The method for logging of claim 6 further comprising generating an electrical signal representative medium time of the total of said electrical pulses within said third time interval.

9. The method for logging of claim 6 further comprising generating an electrical signal representative of a weighted average time of the total of said electrical pulses within said third time interval.

10. Apparatus for logging the formations surrounding an earth borehole, comprising:
a pulsed source for emitting bursts of high energy neutrons;
a radiation detector for detecting radiation emanating from said formations;
circuit means for measuring said detected radiations during first and second time intervals following a burst of neutrons from said source;
circuit means for generating time-separated electrical pulses indicative of said detected radiations during a third fixed time duration interval following a subsequent burst from said source; and
circuit means for automatically controlling the starting time of said third measurement interval in accordance with said measurement from said first and second intervals.

11. The apparatus of claim 10 wherein said third time interval is automatically controlled to start from between 200–400 microseconds following said subsequent neutron burst.

12. The apparatus of claim 11 wherein said third time interval is of 600 microseconds in duration.

13. The apparatus of claim 12 wherein said first and second time intervals are contiguous and of equal duration.

14. The apparatus of claim 13 wherein said first time interval is from between 400–600 microseconds after said burst of high energy neutrons and said second time interval is from between 600–800 microseconds following said burst of high energy neutrons.

15. The apparatus of claim 14 further comprising deriving a ratio of said measured radiations during said first and second intervals, said ratio being substantially representative of the decline of the neutron population in said formations.

16. The apparatus of claim 15 further comprising generating an electrical signal representative of the arithmetic mean time of the total of said electrical pulses within said third time interval.

17. The apparatus of claim 15 further comprising generating an electrical signal representative medium time of the total of said electrical pulses within said third time interval.

18. The apparatus of claim 15 further comprising generating an electrical signal representative of a weighted average time of the total of said electrical pulses within said third time interval.

* * * * *